(12) United States Patent
Ding et al.

(10) Patent No.: US 10,058,566 B2
(45) Date of Patent: Aug. 28, 2018

(54) SULFATED POLYGULONIC ACID POLYSACCHARIDE OR PHARMACEUTICAL SALT THEREOF, PREPARATION METHOD THEREFOR AND USE THEREOF

(71) Applicant: SHANGHAI INSTITUTE OF MATERIA MEDICA CHINESE ACADEMY OF SCIENCES, Shanghai (CN)

(72) Inventors: Jian Ding, Shanghai (CN); Jing Ai, Shanghai (CN); Yi Chen, Shanghai (CN); Xun Huang, Shanghai (CN)

(73) Assignee: SHANGHAI INSTITUTE OF MATERIA MEDICA CHINESE ACADEMY OF SCIENCES, Shanghai (CN)

(*) Notice: Subject to any disclaimer, the term of this patent is extended or adjusted under 35 U.S.C. 154(b) by 151 days.

(21) Appl. No.: 14/901,297

(22) PCT Filed: Jul. 2, 2014

(86) PCT No.: PCT/CN2014/081472
§ 371 (c)(1),
(2) Date: Dec. 28, 2015

(87) PCT Pub. No.: WO2015/000411
PCT Pub. Date: Jan. 8, 2015

(65) Prior Publication Data
US 2016/0367591 A1    Dec. 22, 2016

(30) Foreign Application Priority Data

Jul. 2, 2013 (CN) .......................... 2013 1 0275323

(51) Int. Cl.
*A61K 31/737* (2006.01)
*C08B 37/00* (2006.01)
*C08L 5/00* (2006.01)

(52) U.S. Cl.
CPC ........ *A61K 31/737* (2013.01); *C08B 37/0084* (2013.01); *C08L 5/00* (2013.01)

(58) Field of Classification Search
CPC ...... C08B 37/0084; C08L 5/00; A61K 31/737
USPC .......................................................... 514/54
See application file for complete search history.

(56) References Cited

U.S. PATENT DOCUMENTS 4,689,322 A    8/1987    Kulbe et al.

FOREIGN PATENT DOCUMENTS

| CN | 1132209 A | 10/1996 |
|---|---|---|
| CN | 1473836 A | 2/2004 |
| CN | 1544475 A | 11/2004 |
| CN | 101691410 A | 4/2010 |
| CN | 102743409 A | 10/2012 |
| JP | H06025304 A | 2/1994 |
| JP | 2001-500184 A | 1/2001 |
| JP | 2007-230902 A | 9/2007 |
| JP | 2008-27767 A | 2/2008 |
| JP | 2013-525269 A | 6/2013 |
| WO | 1998/011141 A1 | 3/1998 |
| WO | 2011/109900 A1 | 9/2011 |

OTHER PUBLICATIONS

Zhao et al, Carbohydrate Polymers, 2007, 69, 272-279.*
The Merck Manual, 1992, p. 1274.*
Trisha Gura's article in Science, Nov. 1997, pp. 1041-1042.*
Zhao, et al., "Effects of low-molecular-weight polyguluronate sulfate on experimental urolithiasis in rats", Urol Res, 35;301-306, 2007.
Zhao, et al., "Preparation of low-molecular-weight polyguluronate sulfate and its anticoagulant and anti-inflammatory activities", Carbohydrate Polymers, Applied Science Publishers, ltd., Barking, GB, 69(2):272-279, May 7, 2007.
Zhao, "Studies on Preparation Structure and Activities of Polyguluronate Sulfate and Its Oligosaccharides" Doctoral Dissertation, Ocean University of China, pp. 1-152, Feb. 15, 2009.
Japanese Office Action for Application No. 2016-522246, dated May 23, 2018. 9 pages.

* cited by examiner

*Primary Examiner* — Ganapathy Krishnan
(74) *Attorney, Agent, or Firm* — McCarter & English, LLP; Steven G. Davis; Wei Song (57) ABSTRACT

A polygulonic acid sulfate or pharmaceutically acceptable salt thereof, preparation method therefor and use thereof in the preparation of tumor growth and/or metastasis inhibitors are disclosed. The polygulonic acid sulfate or pharmaceutically acceptable salt thereof of the present invention can be used in the preparation of any one or more of tumor growth inhibitors, tumor metastasis inhibitors, angiogenesis inhibitors, heparanase inhibitors, C-Met enzyme inhibitors, microtubule polymerization inhibitors, actin-depolymerizing factor activity inhibitors and actin-aggregation inhibitors.

14 Claims, 9 Drawing Sheets

Control group           PGAS 20 mg/kg

SULFATED POLYGULONIC ACID POLYSACCHARIDE OR PHARMACEUTICAL SALT THEREOF, PREPARATION METHOD THEREFOR AND USE THEREOF

RELATED APPLICATIONS

This application is the U.S. National Stage of PCT International Application No. PCT/CN2014/081472, filed Jul. 2, 2014, which claims the benefit of Chinese Patent Application No. CN201310275323.7, filed Jul. 2, 2013. The entire teachings of each of the aforementioned applications are incorporated herein by reference.

FIELD OF THE INVENTION

The present invention relates to the field of medicine, and in particular, to a polygulonic acid sulfate or pharmaceutically acceptable salt thereof, preparation method therefor and use thereof in the preparation of tumor growth and/or metastasis inhibitors.

DESCRIPTION OF RELATED ART

Tumors pose a serious threat to human life and health. Malignant tumors have become the number one cause of death in urban residents and number two cause in rural residents, and rank first in mortality among various diseases. Tumor metastasis is one sign of malignance, and metastasis and recurrence of malignant tumors are the major causes of treatment failure. Therefore, finding anti-tumor drugs capable of inhibiting tumor growth and metastasis is the current focus of attention.

According to recent studies, saccharides not only are one class of important structural constitutions and energy sources, but also have important biological functions. They are involved in cell-cell recognition and signaling and are considered to be a class of important signal molecules in addition to nucleic acids in an organism. Also, because they are often the key factors for signal recognition on cell surfaces, antibody-antigen reactions, cell signal transduction and sensing, more and more interest are drawn to the research of active polysaccharides having biological activities. However, due to the complex structure and the difficulties in separation and structural characterization of saccharides, to date, only coriolus versicolor polysaccharides, polyporus polysaccharides, mushroom polysaccharides, schizophyllan polysaccharides, Poria cocos polysaccharides and the like are used for clinical purposes. There is a need in the art to obtain more kinds of polysaccharides having biological activities.

SUMMARY OF THE INVENTION

Despite difficulties in structural resolution and preparation of carbohydrates, and the low activity problem of natural sugars, not to mention the practical problem of severe incidences of tumor and difficulties in treatment, the present inventor completed the present invention based on extensive and intensive studies. The present inventor has completed the present invention by reacting polyguluronic acid with a sulfonating agent under appropriate temperature for an appropriate duration to give a sulfated derivative of oligo-guluronic acid, and then adding a reducing agent for reduction, thus obtaining a polygulonic acid sulfate (hereinafter referred to as "PGAS").

Accordingly, one object of the present invention is to provide a polygulonic acid sulfate or pharmaceutically acceptable salt thereof. The polygulonic acid sulfate or pharmaceutically acceptable salt thereof of the present invention has significant inhibition effect on tumor growth and metastasis, and the mechanism of action is associated with its ability of inhibiting heparanase activity, C-Met enzyme activity, angiogenesis, microtubule polymerization, actin depolymerizing factors and the like. Preferably, the present invention provides a polygulonic acid sulfate or pharmaceutically acceptable salt thereof, in which the L-guluronic acid units are connected through 1,4-glycosidic linkage with each other, with a hydroxyl group located at position 1 of the reducing end, and sugar rings completely sulfated at C-2 positions thereof.

Another object of the present invention is to provide a method for preparing a polygulonic acid sulfate or pharmaceutically acceptable salt thereof. A further object of the present invention is to provide a use of a polygulonic acid sulfate or pharmaceutically acceptable salt thereof in the preparation of tumor growth and/or metastasis inhibitors.

Still another object of the present invention is to provide a pharmaceutical composition comprising a therapeutically effective amount of a polygulonic acid sulfate or pharmaceutically acceptable salt thereof according to the present invention.

Yet another object of the present invention is to provide a method for treating tumors.

According to one aspect of the present invention, a polygulonic acid sulfate or pharmaceutically acceptable salt thereof having a structure of the following general formula (I) is provided:

(I)

in the general formula (I), n represents 0 or an integer of 1-23, $R_1$ is $SO_3H$, $R_2$, independent of one another, is H or $SO_3H$, provided that the degree of sulfation calculated as the sulfur content of the polygulonic acid sulfate is 5 to 20 weight %.

In the polygulonic acid sulfate or pharmaceutically acceptable salt thereof represented by the general formula (I) of the present invention, the polygulonic acid is formed from L-guluronic acids by 1,4-glycosidic linkage, with a hydroxyl group located at position 1 of the reducing end, and sugar rings completely sulfated at C-2 position thereof and partially sulfated at C-3 position thereof.

In the general formula (I) above, n is 0 or an integer of 1-23, for example, 0, 1, 2, 3, 4, 5, 6, 7, 8, 9, 10, 11, 12, 13, 14, 15, 16, 17, 18, 19, 20, 21, 22 or 23; preferably, n is an integer of 2-13, more preferably, n is 3, 4, 5, 6, 7, 8, 9 or 10, and most preferably, n is 4, 5, 6, 7 or 8. Preferably, the sulfur content is 7-15 weight %, more preferably 9-13 weight %.

In the present invention, better biological effects are obtained using tetrasaccharide to dodecasaccharide (particularly hexasaccharide to decasaccharide) and/or when the sulfur content is 7-15 weight % (particularly 9-13 weight %), probably because these polysaccharides are more easily recognized and accepted by body cells.

In the present invention, the pharmaceutically acceptable salts of the polygulonic acid sulfates may be, for example, sodium, potassium, calcium or magnesium salts of these compounds, with sodium salts being preferred. The pharmaceutically acceptable salts may be prepared by conventional methods.

According to another aspect of the present invention, a method for preparing the polygulonic acid sulfate or pharmaceutically acceptable salt thereof is provided, which comprises:

reacting a polyguluronic acid as shown in the following structural formula (II) with a sulfonating reagent, followed by reduction via a reducing agent to give the polygulonic acid sulfate as shown in the general formula (I), (II)

in the formula (II), m represents 0 or an integer of 1-48;

(I)

In the general formula (I), n, $R_1$ and $R_2$ are as defined above.

In the present invention, preferably, the sulfonating reagent may be chlorosulfonic acid; preferably, the sulfonating temperature may be 45-85° C., more preferably 60-75° C., and the reaction time may be 1.5-4.5 hours, more preferably 2-3.5 hours, most preferably 3 hours; preferably, the reducing agent is sodium borohydride, sodium cyanoborohydride, nickel-hydride reagents, halogen-based reducing agents, or the like.

A further aspect of the present invention provides use of a polygulonic acid sulfate or pharmaceutically acceptable salt thereof in the preparation of tumor growth and/or metastasis inhibitors.

In the present invention, the term "tumors" refers to any form of tumors including malignancies, and for example, may be liver cancer, stomach cancer, colorectal cancer, lung cancer, breast cancer, pancreas cancer, kidney cancer, bladder cancer, prostate cancer, melanoma, brain cancer and the like.

In the present invention, preferably, the polygulonic acid sulfate or pharmaceutically acceptable salt thereof can be used as tumor growth inhibitors, tumor metastasis inhibitors, angiogenesis inhibitors, heparanase inhibitors, C-Met enzyme inhibitors, microtubule polymerization inhibitors, actin-depolymerising factor activity inhibitors and/or actin-aggregation inhibitors.

According to still another aspect of the present invention, a pharmaceutical composition is provided, comprising a therapeutically effective amount of a polygulonic acid sulfate or pharmaceutically acceptable salt thereof of the present invention. Preferably, the active component in the pharmaceutical composition is consisted of one or more polygulonic acid sulfates or pharmaceutically acceptable salts thereof of the present invention. In another implementation, in addition to the polygulonic acid sulfate or pharmaceutically acceptable salt thereof of the present invention, the pharmaceutical composition of the present invention may comprise one or more anti-tumor drugs or anti-tumor adjuvant drugs as active component.

In the present invention, preferably, the pharmaceutical composition may further comprise a pharmaceutically acceptable carrier. The pharmaceutically acceptable carrier may be those commonly used in the art.

In the present invention, preferably, the pharmaceutical composition may be used as tumor growth inhibitors.

In the present invention, preferably, the pharmaceutical composition may be used as tumor metastasis inhibitors.

In addition, preferably, the pharmaceutical composition may be used as angiogenesis inhibitors, heparanase inhibitors, C-Met enzyme inhibitors, microtubule polymerization inhibitors, actin-depolymerising factor activity inhibitors and/or actin-aggregation inhibitors.

According to still another aspect of the present invention, a method for treating tumors is provided, comprising administrating a therapeutically effective amount of a polygulonic acid sulfate or pharmaceutically acceptable salt thereof of the present invention to a subject in need of treatment.

In the present invention, the term "effective amount" may refer to an amount effective, at dosages and for periods of time necessary, to achieve a desired result. This effective amount may vary according to factors such as, type of the disease, symptoms of the disease when treated, structure of a specific target organ being administered, size of the subject, or severity of the disease or condition. An effective amount of a particular compound can be empirically determined by those of ordinary skill in the art without undue experimentation.

In view of the above, it is of great importance to use a polygulonic acid sulfate or pharmaceutically acceptable salt thereof of the present invention in the preparation of a medicament for treating tumors and tumor metastasis with a view to solving the current problem of lack of effective drugs for treating tumors.

DETAILED DESCRIPTION OF THE INVENTION

The present invention will be described below in further detail by embodiments. However, the following embodiments are provided only for illustrative purposes, and the scope of the present invention is not limited thereto.

Materials and Reagents

Polyguluronic acid, purchased from Lan Tai Pharmaceuticals Co. Ltd of Ocean University of China, having a weight average molecular weight of 10000 Da with respect to dextran. Formamide, chlorosulfonic acid, etc., provided by Sinopharm Group Chemical Reagent Company, A.R. grade. Dextran molecular weight standard, purchased from Fluka Company. Doxorubicin injection (Adriamycin, ADM), manufactured by Zhejiang Haimen Pharmaceutical Factory, Zhejiang health medicine accurate (1996) No. 135501, content: 10 mg/vial, solvent: normal saline, formulation: diluted to a desired concentration with normal saline prior to each administration. TSK gel2000SWXL, TSK gel G3000SWXL column, available from TOSOH Company of Japan; Bio-Gel-P6, Bio-Gel-P10, from Bio-Rad Company; Sephadex G-10, Sepharose CL-4B, from Pharmacia Company; tubulin, actin, purchased from SIGMA Company.

Instruments

NEXUS-470 intelligent infrared spectrometer, from NICOLET Company; DPX-300 NMR spectrometer, from Bruker Company; Gel Permeation Chromatography (GPC), from Beijing Longzhida Co., Ltd.; UV-2102 ultraviolet and visible spectrophotometer, from Unocal Corporation, US.

Experimental Animals

Nude mice, BALB/cA, 18-22 g, provided by Shanghai Institute of Materia Medica, Chinese Academy of Sciences; $C_{57}BL/6$ mice, 6-7 weeks, provided by Shanghai Animal Center, Chinese Academy of Sciences;

Fresh eggs, purchased from Shanghai Shenbao Chicken Farm.

Example 1: Preparation of Polygulonic Acid Sulfate (PGAS)

3 ml chlorosulfonic acid was added dropwise to 10 ml formamide while maintaining a temperature below 5° C. After 20 min of reaction, 1 g polyguluronic acid was added and reacted at a temperature of 65-70° C. for 3 hours. 2 volumes of 80% ethanol solution was added to the reaction product and agitated repeatedly, to give a viscous substance. Additional 80% ethanol solution was added and the steps above were repeated 2 times. The solution was decanted and water was added to give a viscous substance. The viscous substance was adjusted with a 1% $Na_2CO_3$ solution to a pH of 7.0 and subjected to alcohol precipitation with 2 volumes of a 95% ethanol solution. The resulting precipitate was dried at a temperature of 50-60° C. to give a sulfated derivative of the polyguluronic acid. The derivative was formulated into a 4 mg/ml sodium acetate solution (pH7.0) and to the solution sodium borohydride was added to 50 mM. The reaction was conducted at a temperature of 30-40° C. for 30 min and terminated with an ice bath. The pH was adjusted with 0.1M acetic acid, unreacted sodium borohydride was released, and the pH was adjusted to be neutral. The resulting solution was repeatedly precipitated and washed with ethanol, and dried, giving a crude of polygulonic acid sulfate (PGAS). The PGAS crude was formulated into a 10% solution and subjected to precipitation with a 95% ethanol solution. The resulting precipitate was washed with absolute ethanol, dried, and formulated into a 5% solution. The solution was filtered with a 3 μm membrane to remove impurities and de-salted in the Sephadex G-10 column (15×100 cm) with water as a mobile phase and using fraction collection. Eluates were detected with the sulfuric acid-carbazole method, and sugar-containing components were combined, concentrated at reduced pressure, de-salted, and freeze-dried, giving a refined polygulonic acid sulfate.

The sulfur content of the polygulonic acid sulfate prepared above was determined with the oxygen flask combustion method. About 25 mg of a sample was taken, precisely weighted, and subjected to destruction of organics following the oxygen flask combustion method. A 1000 ml combustion flask was used, 0.1 ml concentrated hydrogen peroxide solution and 10 ml water were used as absorbing liquid. Once the generated smoke was completely absorbed, the resulting substance was placed in an ice bath for 15 min, heated to gentle boiling for 2 min, cooled, added with 50 ml ethanol-ammonium acetate buffer (pH3.7), 30 ml ethanol, and 0.3 ml of a 0.1% Alizarin red solution as indicator, and titrated to light orange-red with a barium perchlorate titration solution (0.05 mol/L). 1 ml of the barium perchlorate titration solution (0.05 mol/L) is equivalent to 1.603 mg of S. The test results show that, based on the dried product, the sulfur content of the polygulonic acid sulfate is 11.2 weight %.

4. Molecular Weight and Molecular Weight Distribution of PGAS

The molecular weight of PGAS was determined with the GPC method. The detection was performed using the Refractive Index Detector, with dextran from Fluka Company as a molecular weight standard, TSK gel2000SWXL column as a chromatographic column, and an aqueous solution containing 0.2% sodium azide and 2.84% $Na_2SO_4$ as a mobile phase, at a flow rate of 0.5 ml/min, a temperature of 35° C., and an injection volume of 254 µl. It is found that, the weight average molecular weight of PGAS with respect to dextran is 2513 Da, and the determination results of multiple batches of samples show that its weight average molecular weight with respect to dextran is between 1500-8500 Da.

Together, these results confirm that the fraction above is a polygulonic acid sulfate, which has a hydroxyl group at position 1 at the reducing end of polyguluronic acid, and is completely sulfated at C-2 position and partially sulfated at C-3 position, having the following chemical formula (I):

(I)

Example 2: Structural Characterization of Polygulonic Acid Sulfate (PGAS)

The structural characterization was conducted on the saccharide components in the fraction resulting from the preparation of polygulonic acid sulfate above.

1. UV Absorption Spectrum

The polygulonic acid sulfate above was diluted to a suitable concentration, and with distilled water as blank, scanned between 190 nm-400 nm with the UV-2102 ultraviolet-visible spectrophotometer. It is found that the fraction has no specific absorption peak in the ultraviolet region, indicating no conjugated double bond in the structure. However, there is non-specific absorption at 190-200 nm.

2. Infrared Spectroscopy 0.5 mg PGAS was pressed to be KBr pellets, and the infrared spectroscopy was performed with the NEXUS-470 intelligent infrared spectrometer. It was found that, symmetric stretching vibration of hydroxyl groups is present at 3219.53 $cm^{-1}$, symmetric stretching vibration of carbonyl groups in carboxylates is present at 1612.58 $cm^{-1}$, scissoring vibration of hydroxyl groups is present at 1414.33 $cm^{-1}$, symmetric stretching vibration of carbon-oxygen bonds in carboxyl groups is present at 1103.97 $cm^{-1}$, stretching vibration peak of C—O—S is present at 823.30 $cm^{-1}$, and stretching vibration peak of S=O in the sulfate after sulfation is present at 1274.62 $cm^{-1}$, which indicates that the compound has a backbone structure containing carboxyl, hydroxyl and sulfoic groups.

3. NMR Spectroscopy of PGAS

The NMR spectroscopy ($^{13}C$-NMR) of PGAS was determined with Bruker Auance DPX-300 NMR spectrometer. It was found that in the spectrum, non-sulfonated C-2 signal peaks are substantially not seen while non-sulfonated C-3 signal peaks still exist. It is indicated that the hydroxyl groups at position C-2 are relatively completely sulfated, and the hydroxyl groups at position C-3 are only partially sulfated.

in the general formula (I), n, $R_1$ and $R_2$ are as defined above.

Example 3: Separation and Preparation of Components of PGAS

A sample of PGAS prepared above was taken, formulated into a 5% solution, filtered with a 3 µm membrane to remove impurities, and separated on the Bio-Gel-P6 gel column (1.6×180 cm), with 0.2 mol/L $NH_4HCO_3$ as a mobile phase and fractions were collected. Eluates were detected with the sulfuric acid-carbazole method, sugar-containing components were collected and void volume components were further separated on the Bio-Gel-P10 gel column (1.6×180 cm). The resulting products were freeze-dried to give a series of saccharide components of PGAS, which were identified by mass spectrometry. Results confirm the production of di-, tri-, tetra-, penta-, hexa-, hepta-, octa-, nona-, deca-, undeca-, and more saccharide components of PGAS.

In the experiments below, Examples 4-11 use the product prepared in Example 1, while Examples 12 and 13 use the products prepared in Example 3.

Example 4: Evaluation of Tumor Growth Inhibition Efficacy of Polygulonic Acid Sulfate (PGAS)

Human breast cancer MDA-MB-435 cells (from American Type Culture Collection, ATCC, Rockville, Md., USA) in an exponential growth phase at a concentration of $2.5 \times 10^7$ cells/ml were inoculated into the second left mammary fat pad of 4-5-week old female nude mice (BALB/cA, provided by Shanghai Institute of Materia Medica, Chinese Academy of Sciences). When the tumors were grown to the size of 100-200 $mm^3$, the animals were evenly divided according tumor volumes into a negative control group, a doxorubicin injection (Adriamycin, ADM) treatment group (positive control group), and 5 mg/kg and 20 mg/kg PGAS treatment groups (PGAS experimental groups), 20 mice/group. The PGAS experimental groups and the positive control group were dosed once per week by intravenous injection for 7 continuous weeks, and the negative control group was dosed with an equal amount of normal saline. In the experiments, a vernier caliper was used to measure the diameter of tumors twice a week, and the tumor volume (V) was calculated following the formula below:

$$V = \frac{1}{2} \times a \times b^2$$

in which, a and b represent the length and the width of tumors, respectively. The relative tumor volume (RTV) was calculated based on the measured results, using the calculation formula: $RTV_t = V_t/V_o$; in which, $V_0$ is the measured tumor volume when animals were divided to different dosing (i.e. $d_0$), and Vt is the tumor volume on the day of measurement. The pharmacodynamic evaluation indicator of anti-tumor activity is relative tumor proliferation rate T/C (%), the calculation formula of which is as follows:

$$T/C(\%) = \frac{T_{RTV}}{C_{RTV}} \times 100\%$$

$T_{RTV}$: RTV of treatment group; $C_{RTV}$: RTV of negative control group. Efficacy Evaluation: T/C %>60% means ineffective; T/C %≤60% with statistical significance of P<0.05 means effective.

The animals were sacrificed 1 week after discontinuation of dosing. Lung tissues were fixed in Bouin's solution (saturated picric acid:formaldehyde:glacial acetic acid=75: 25:5) for over 24 hours, and soaked in absolute ethanol until lung metastases appeared as white nodes, and lung tissues recovered the normal color. The number of lung metastasis nodes per lung was observed and recorded under a dissecting microscope. A part of orthotopic tumor tissues were placed in liquid nitrogen, freeze-stored for extraction of total RNA and protein. A part of lungs and orthotopic tumor tissues were fixed in 10% formalin, and angiogenesis in tumor tissues was determined by H&E staining and immunohistochemistry.

Figure 1:
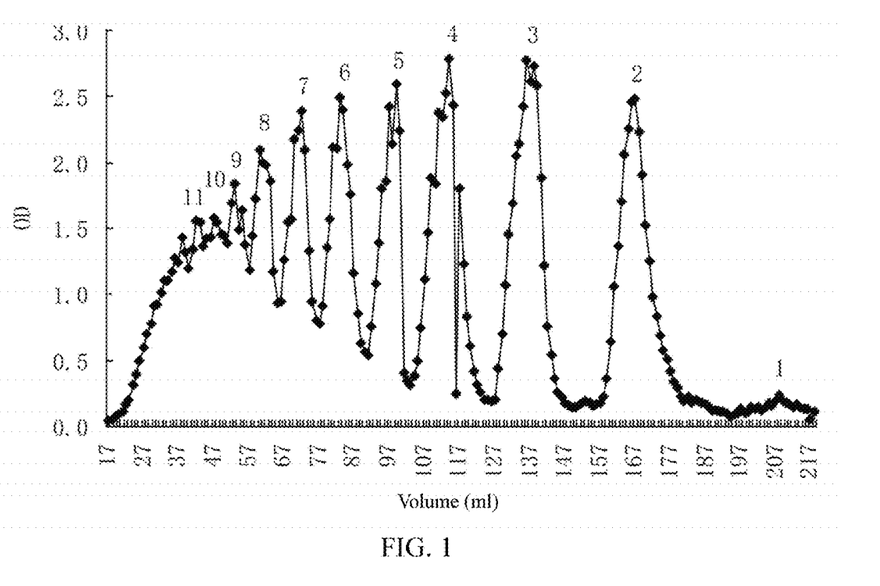
FIG. 1 shows column separation result for respective components of the polygulonic acid sulfate of the present invention.
Figure 2:
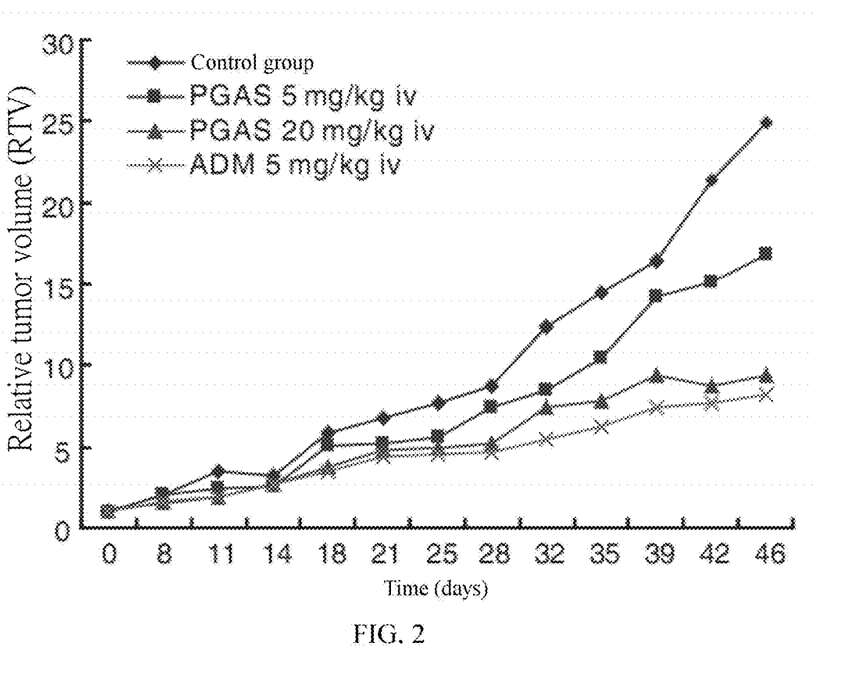
FIG. 2 shows the inhibition effect of a polygulonic acid sulfate of the present invention on the growth of human breast cancer MDA-MB-435 orthotopic xenografts.
Figure 3:
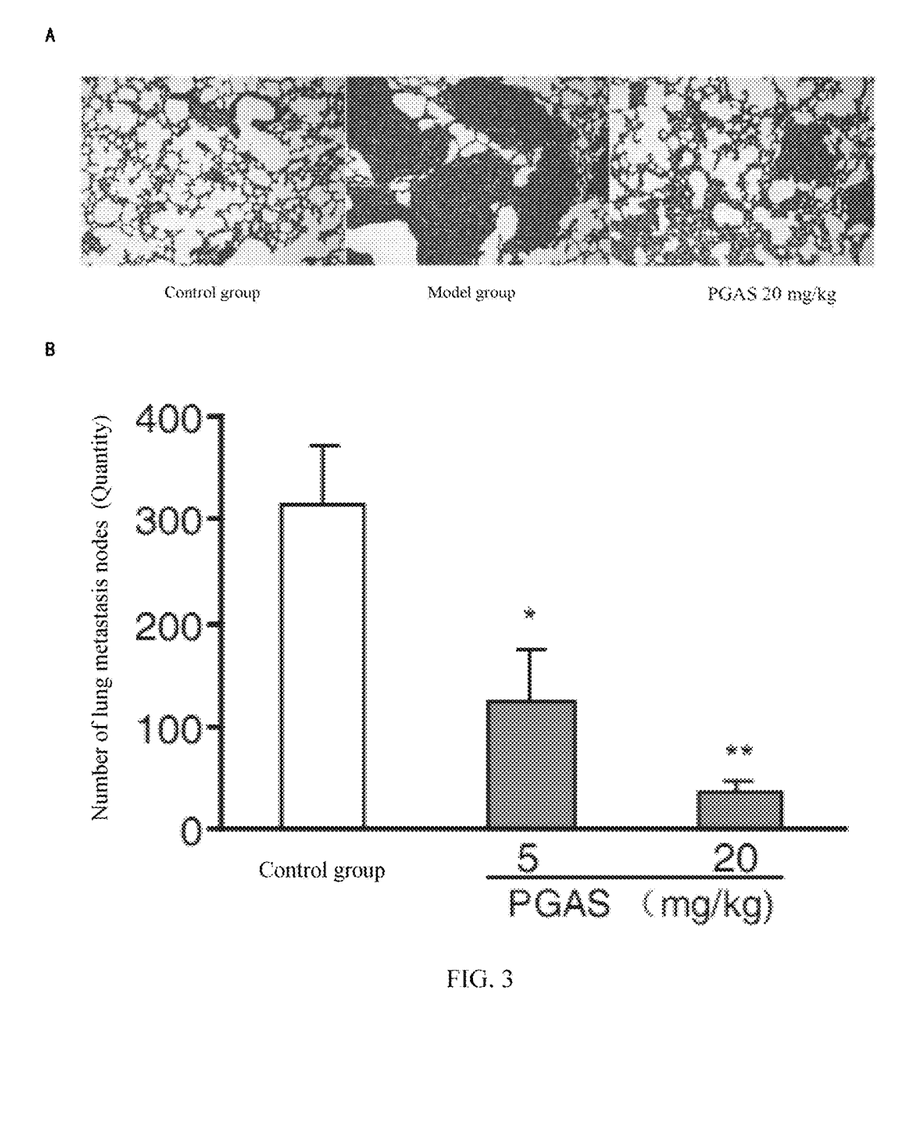
FIG. 3 shows the inhibition effect of a polygulonic acid sulfate of the present invention on lung metastasis of human breast cancer MDA-MB-435 orthotopic xenografts. Panel A shows a typical picture (magnification: 200×) of metastasis in the lung by H&E staining; panel B is a quantitative view of the inhibition effect of PGAS on lung metastasis of MDA-MB-435 orthotopic xenografts. The data in the figure is expressed as mean±SD in one typical experiment. *P<0.05, **P<0.01, treatment group v.s. control group.
Figure 4:
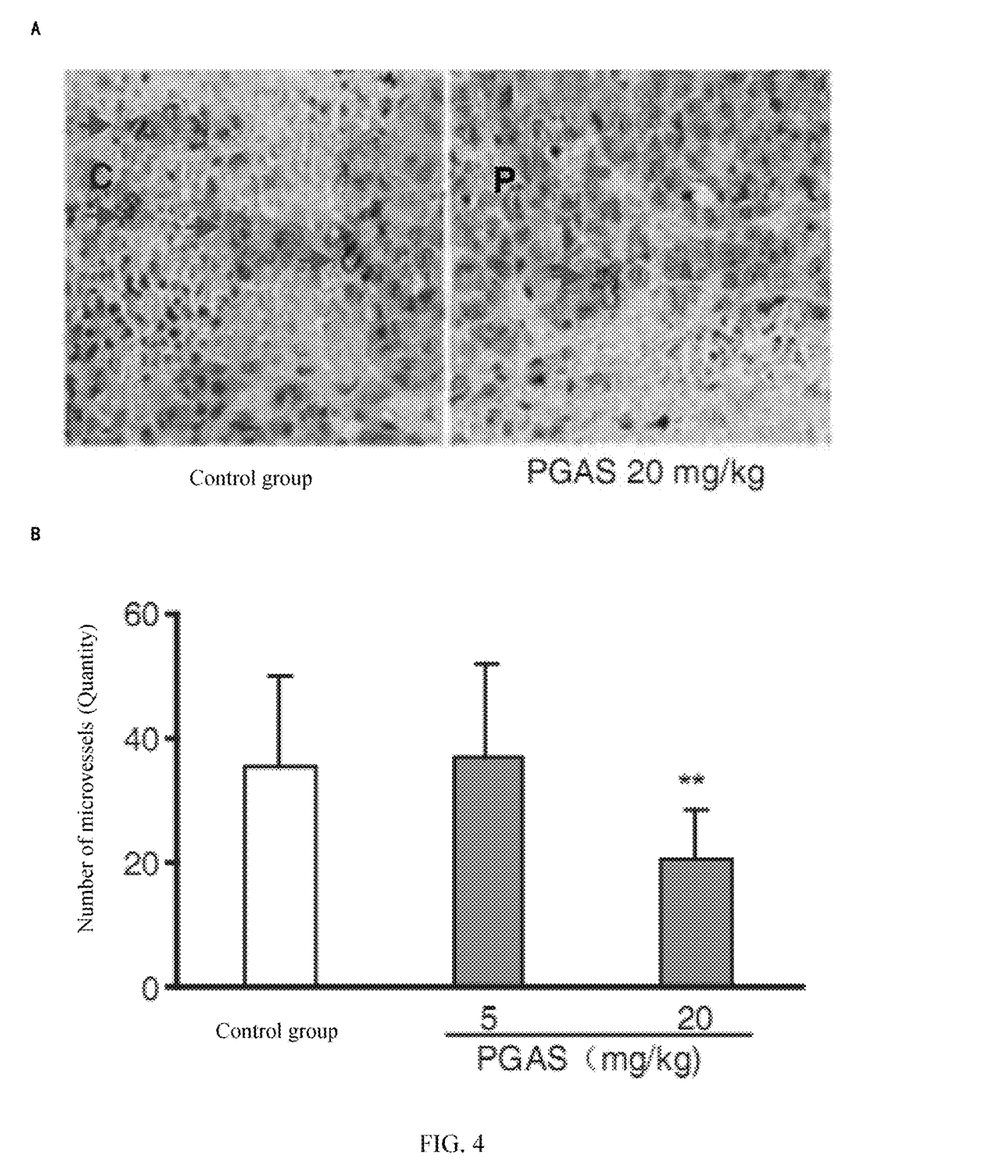
FIG. 4 shows the angiogenesis inhibition effect of a polygulonic acid sulfate of the present invention on human breast cancer MDA-MB-435 orthotopic xenografts. Panel A shows a typical picture of CD31 staining with arrows pointing to positive staining (magnification: 200×) (in Panel A: "C" is a control group, "P" is a PGAS treatment group); panel B is a quantitative view of the angiogenesis inhibition effect of PGAS on human breast cancer MDA-MB-435 orthotopic xenografts. The data in the figure is expressed as mean±SD in one experiment. **P<0.01, treatment group v.s. control group.

It was found that on 15-20 days after tumor inoculation, the human breast cancer MDA-MB-435 xenografts have grown to around 100-200 mm³, with an inoculation success of 100%; on weeks 8-9 after inoculation, a large number of metastases appear in lung tissues of the tumor-bearing nude mice, with a metastasis rate of 100%. At this point of time, the animals are sacrificed and subjected to anti-tumor effect evaluation. PGAS treatment was performed by intravenous injection once per week for 7 continuous weeks. The 5 mg/kg PGAS treatment group shows the ability of inhibiting the growth of orthotopic tumors, but the tumor inhibition effect is insignificant, with a T/C value of 67.3%; the 20 mg/kg PGAS treatment group shows the ability of significantly inhibiting the growth of human breast cancer MDA-MB-435 orthotopic xenografts in nude mice, with a T/C value of up to 37.6%. The positive control drug ADM shows the ability of significantly inhibiting the growth of human breast cancer MDA-MB-435 orthotopic tumors, and the 5 mg/kg ADM treatment group has a T/C value of 21.8%. This shows that PGAS can significantly inhibit the growth of human breast cancer MDA-MB-435 orthotopic xenografts (FIG. 2). Under the dosing regimen of 5 mg/kg and 20 mg/kg by intravenous injection once per week for 7 continuous weeks, the inhibition rates of PGAS on lung metastasis of human breast cancer MDA-MB-435 orthotopic xenografts are 60.2% and 88.4%, respectively. The inhibition rate of doxorubicin (5 mg/kg) on lung metastasis is 89.8%. This shows that PGAS can significantly inhibit the lung metastasis of human breast cancer MDA-MB-435 orthotopic xenografts (FIG. 3). Further, the effect of PGAS on angiogenesis in vivo was evaluated by immunohistochemical staining. The detection of the endothelial cell specific marker CD31 shows that a large number of small vessels are generated in human breast cancer MDA-MB-435 orthotopic xenografts. There is no significant change in number of small vessels in xenografts for the 5 mg/kg PGAS treatment group as compared with the control group, whereas there is a significant decrease in number of small vessels in xenografts in the 20 mg/kg PGAS treatment group as compared with the control group, with an inhibition rate of 42.1%. This shows that PGAS can significantly inhibit the angiogenesis in human breast cancer MDA-MB-435 orthotopic xenografts (FIG. 4).

Example 5: Evaluation of Tumor Metastasis Inhibition Efficacy of Polygulonic Acid Sulfate (PGAS)

Figure 5:
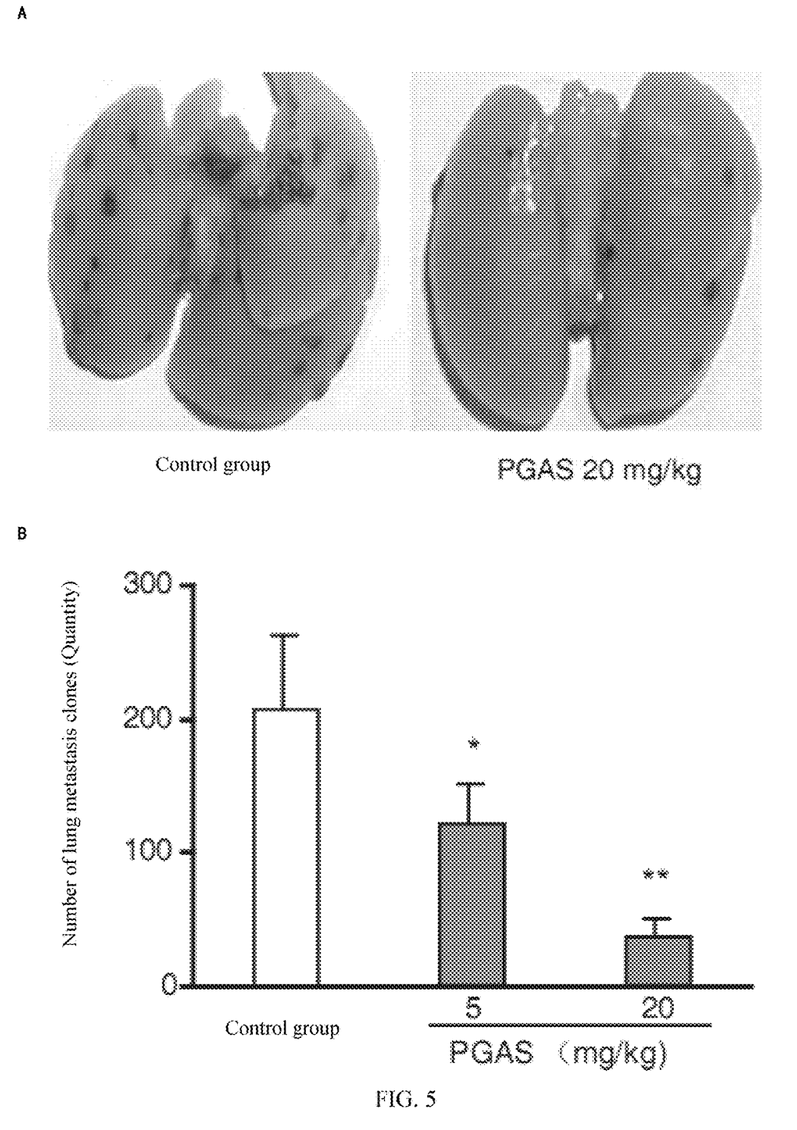
FIG. 5 shows the inhibition effect of a polygulonic acid sulfate of the present invention on experimental lung metastasis of murine melanoma $B_{16}F_{10}$ cells. Panel A shows a typical picture of metastases in the lung; panel B is a quantitative view of the inhibition effect of PGAS on experimental lung metastasis of $B_{16}F_{10}$. The data in the figure is expressed as mean±SD in one typical experiment. Similar results may be obtained from at least two independent experiments. *P<0.05, **P<0.01, treatment group v.s. control group.

6-7-week old C57BL/6 mice (provided by Shanghai Animal Center, Chinese Academy of Sciences) were randomly divided into a normal saline negative control group, and a 5 mg/kg PGAS treatment group and a 20 mg/kg PGAS treatment group, 10 animals/group. Murine melanoma $B_{16}F_{10}$ cells (from American Type Culture Collection, ATCC, Rockville, Md., USA) at an exponential growth phase in a concentration of $2.5 \times 10^6$ cells/ml were inoculated into the tail vein of the mice. 20 min before cell inoculation, the PGAS groups were dosed once by intraperitoneal (i.p.) injection, and the negative control group was dosed with an equal amount of normal saline. 11 days later, lungs were removed from mice, and the lung tissues were fixed in Bouin's solution (saturated picric acid:formaldehyde:glacial acetic acid=75:25:5) for over 24 hours. The number of lung metastasis nodes per lung was observed and recorded under a dissecting microscope. Alternatively, such observation was performed after the lung tissues were further soaked in absolute ethanol for two days until the lung tissues recovered the normal color. It was found that, 11 days after inoculation, a large number of metastases appear in lung tissues of the mice, with a metastasis rate of 100%, and in the dosing regimen of single i.p. injection, the 5 mg/kg PGAS treatment group shows significant tumor metastasis inhibition, with an inhibition rate of up to 40.81%, and the 20 mg/kg PGAS treatment group shows more significant inhibition on lung metastasis of melanoma $B_{16}F_{10}$ cells, with an inhibition rate of up to 82.20%. The results show that PGAS can significantly inhibit the lung metastasis of melanoma $B_{16}F_{10}$ cells (FIG. 5).

The inventor further studied the mechanism of action of PGAS.

Example 6: Test of Angiogenesis Inhibition by PGAS

Figure 6:
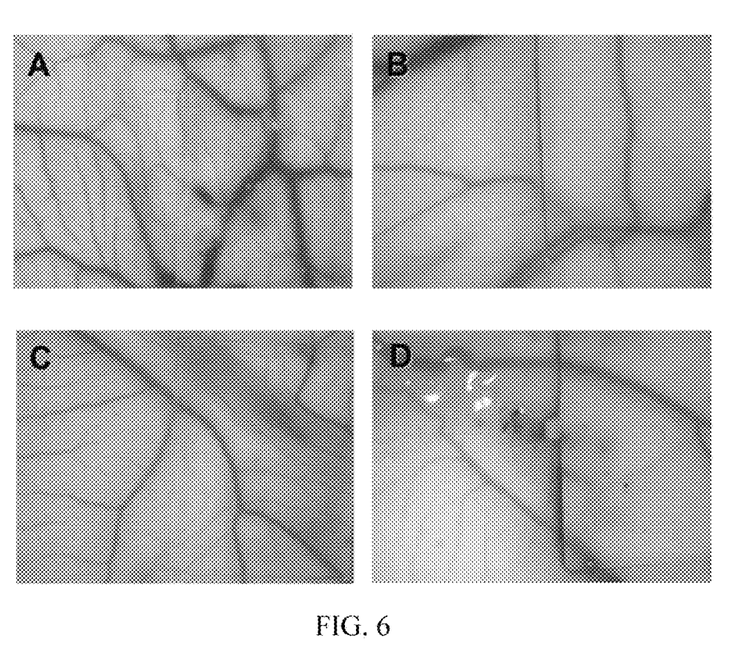
FIG. 6 shows the inhibition effect of a polygulonic acid sulfate of the present invention on neovascularization of chicken embryo chorioallantoic membrane (CAM). Panel A shows a dissolvant control group; panel B shows a 200 μg/egg PGAS group; panel C shows a 400 μg/egg PGAS group; panel D shows a 800 μg/egg PGAS group (magnification: 40×).

Fresh eggs (purchased from Shanghai Shenbao Chicken Farm) were placed in an incubator Roll-X base (Lyon Electric Company, CA, USA) at 39° C. and at 50% humidity (the gas chamber side up). After continuous incubation for 7 days, the eggs were illuminated to identify whether the chicken embryo were alive and the position of chorioallantoic membrane was determined and marked. One small hole was made at the air sac end of the eggs, and the chick embryo was horizontally placed (the chorioallantoic membrane up). The air sac was gently sucked with a rubber pipette bulb, so that the chorioallantoic membrane was collapsed and separated from the eggshell, and allowed to stand for a period of time. Then, an open window position of 1 cm² was made over the chick embryo, and the open window was ground and cut out with a scissor, the dust was blown off the eggshell, the eggshell at the open window was peeled away, and the chorioallantoic membrane was clearly visible. Gelatin sponges having a size of 0.25×0.25×0.25 (length×width×height) cm³ were treated with 10 μl PGAS at a final concentration of 200, 400, 800 μg/egg and a vehicle control, and then gently placed at the site in the chorioallantoic membrane without large vessels. The small window was sealed with sterile transparent tape, and the eggs were further incubated for 48 hours. The tape was peeled away for observation, the photographs were taken (magnification: 40×), and the inhibition effect of PGAS on angiogenesis of chicken embryo chorioallantoic membrane was evaluated. It was found that (FIG. 6), in the chorioallantoic membrane adjacent to the sponge containing PGAS, the vessel density is significantly reduced, and the tendency of concentration-dependent inhibition was exhibited. This shows that PGAS has the angiogenesis inhibition effect.

Example 7: Test of Heparanase Activity Inhibition by PGAS

Figure 7:
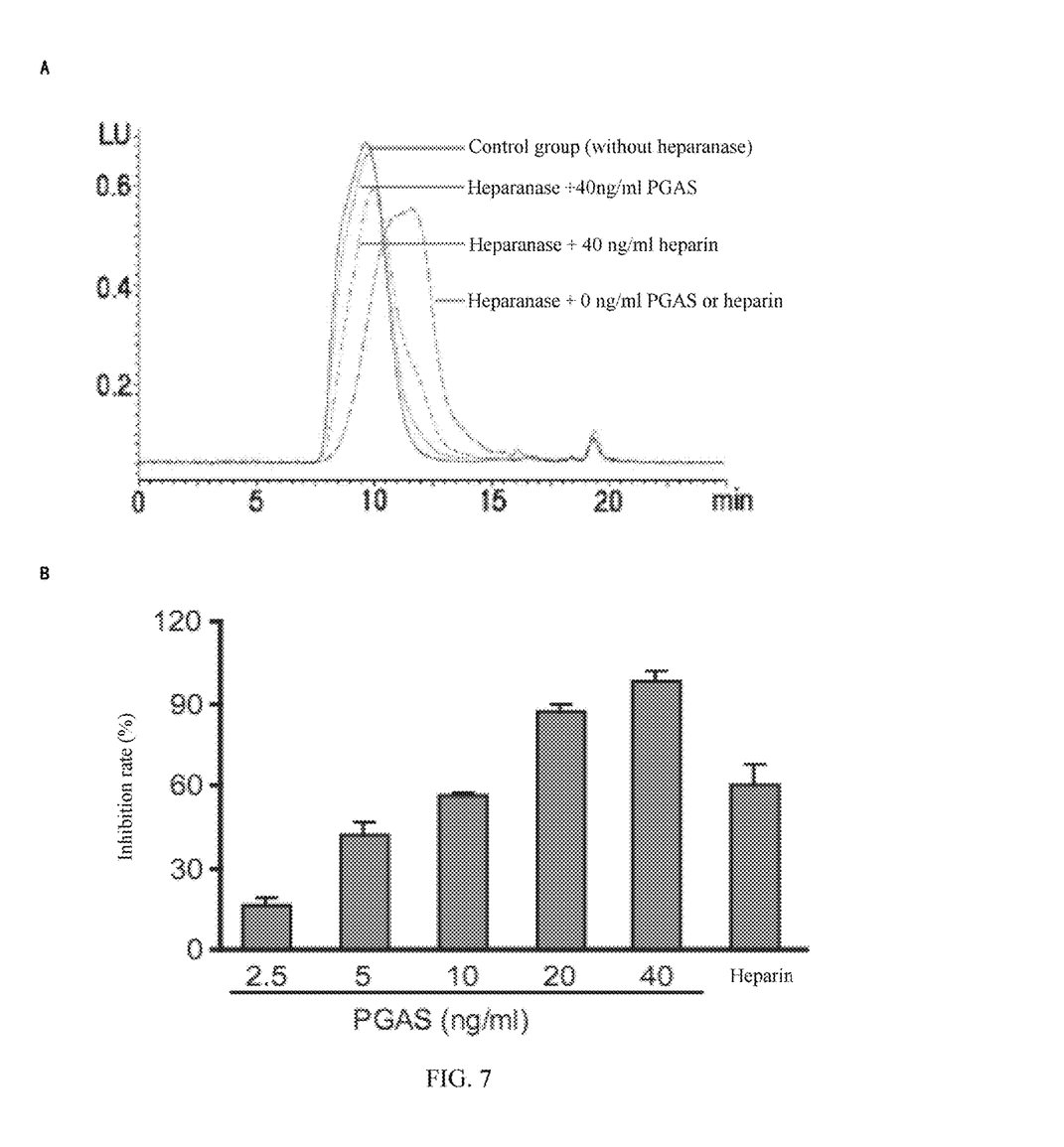
FIG. 7 shows the inhibition effect of a polygulonic acid sulfate of the present invention on heparanase activity. Panel A shows HPLC spectrum indicating the inhibition of heparanase activity of a polygulonic acid sulfate of the present invention; panel B shows the inhibition rate of heparanase activity of a polygulonic acid sulfate of the present invention, calculated from the results of the panel A spectrum above.

Serum-free insect expression system and affinity column purification system of heparanase were established using cDNA of human heparanase obtained from human placenta by PCR amplification and gene recombination, and highly active heparanase having a purity of 95% or greater was obtained. To 150 μL of a reaction buffer (50 mM sodium acetate, pH4.2), 0.5 μg FITC-HS (fluorescein isothiocyanate-labeled heparan sulfate) and heparanase at a final concentration of 25 ng/ml, and also PGAS at various concentrations was added, and reacted at 37° C. for 3 h. After 5 min at 100° C., the centrifugation was performed at 10000 rpm for 20 min to pellet insoluble materials. The supernatant was filtered with a 0.45 μm filter membrane and then injected onto the TSK gel G3000SWXL column at a loading of 20 μl, using a buffer 50 mM Tris/150 mM NaCl, pH7.5, and a flow rate of 0.8 ml/min. The fluorescence intensity of the FITC-HS product was detected with a fluorescence detector (Ex: 485 nm, Em: 538 nm). The relative activity of the enzyme was evaluated by the decrease of forward half area of the intact FITC-HS peak, to determine the effect of PGAS on heparanase activity. It was found that, PGAS inhibits heparanase activity in a dose-dependent manner, with an $IC_{50}$ of 6.55 ng/ml, and when the dose is 40 ng/ml, the activity is better than that of the positive control heparin (FIG. 7).

Example 8: Test of C-Met Enzyme Activity Inhibition by PGAS

Enzyme reaction substrate Poly (Glu, Tyr) was coated on a microtiter plate, ATP solution and polygulonic acid sulfate and c-Met enzyme solution with appropriate concentrations were added and were placed on a shaker for reaction at 37° C. for 1 hour. Then, T-PBS diluted PY99 antibody containing 5 mg/ml BSA was added and reacted on the shaker at 37° C. for 0.5 hour. Further, horseradish peroxidase-labeled goat anti-mouse IgG was added and reacted on the shaker at 37° C. for an additional 0.5 hour. Finally, 2 mg/ml OPD developing solution was added, reacted at 25° C. in the dark for 1-10 min, and 2M $H_2SO_4$ was added to terminate the reaction. The absorbance at 490 nm was measured by the microplate reader and the enzyme activity inhibition rate was calculated:

$$\text{Inhibition rate}(\%) = \left(1 - \frac{OD \text{ value of compound} - OD \text{ value of control well without enzyme}}{OD \text{ value of negative control well} - OD \text{ value of control well without enzyme}}\right) \times 100$$

It was found that, the enzyme activity inhibition rate of polygulonic acid sulfate at a concentration of 10 μg/ml on c-Met is 71.1%, indicating that polygulonic acid sulfate has the effect of inhibiting c-Met enzyme activity.

Example 9: Test of Tubulin Polymerization Inhibition by PGAS

Figure 8:
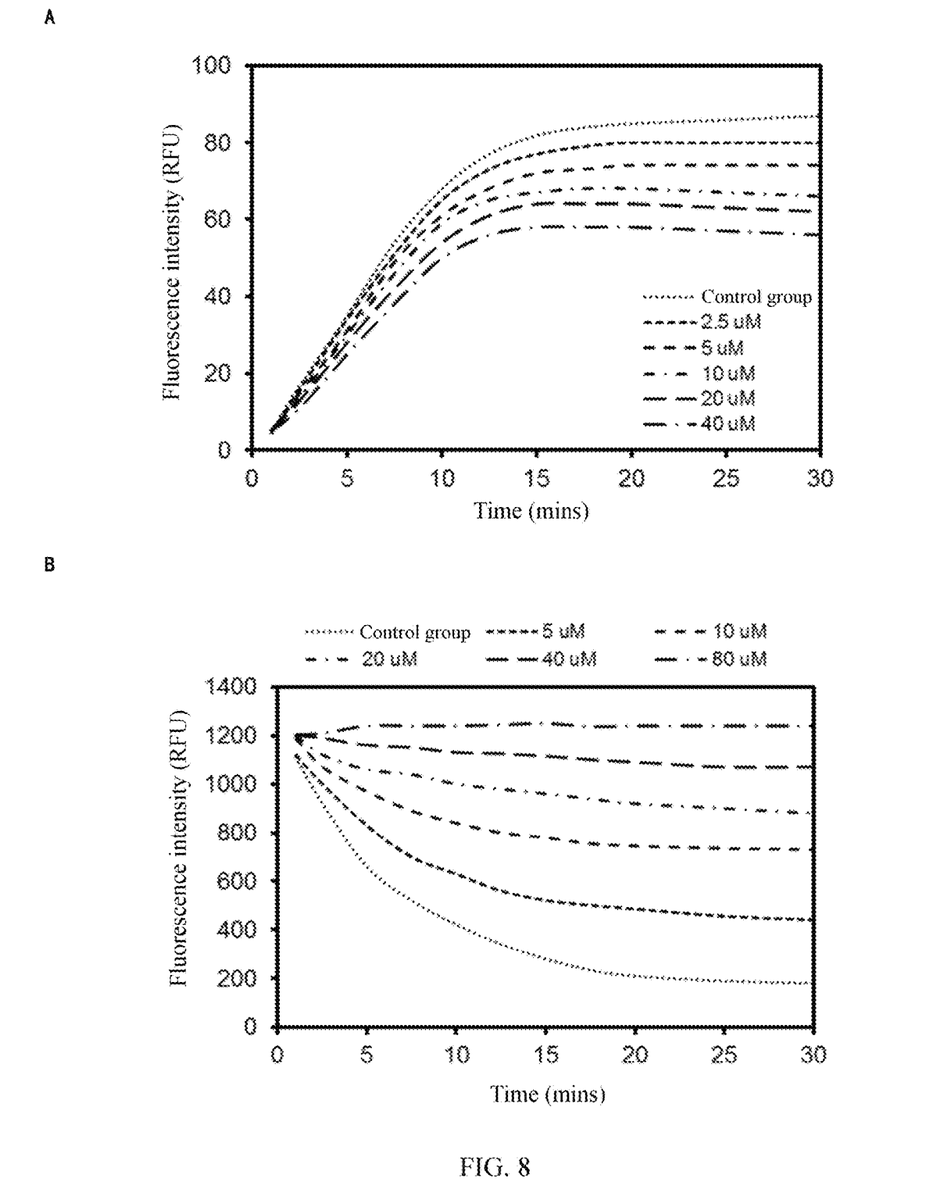
FIG. 8 shows inhibition effect of a polygulonic acid sulfate of the present invention on tubulin polymerization in a cell-free system. Panel A shows time dependency, and panel B shows dose dependency.

10 μl PGAS at various concentrations was added into a 96-well plate and pre-heated at 37° C. for 10 min. Tubulin lyophilized powder was diluted in PEM buffer (100 mM PIPES, 1 mM $MgCl_2$, 1 mM EGTA) plus 1 mM GTP, 5% glycerin to a concentration of 12 μM. 90 μl of this solution was added to the 96-well plate, and a microplate reader was started, the temperature was set at 37° C. and detection wavelength was set at 340 nm. It was thoroughly mixed and read once per min for a continuous 30 min. The results show that PGAS can significantly inhibit the tubulin polymerization in the cell-free system, and when the concentration of PGAS is increased from 2.5 μM to 40 μM, the inhibition rate is increased from 18.26% to 73.44%, which is dose-dependent, with an $IC_{50}$ of 8.58 μM (FIG. 8).

Example 10: Actin Depolymerization Inhibition by PGAS

Figure 9:
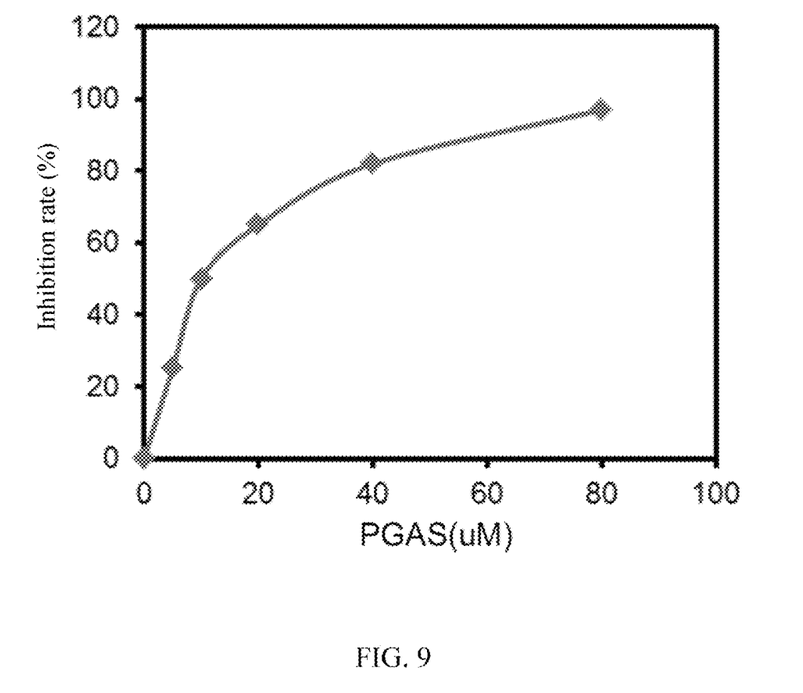
FIG. 9 shows the inhibition effect of a polygulonic acid sulfate of the present invention on actin depolymerization in a cell-free system.

Pyrenyl-labeled actin was added into aggregation buffer (100 mM Tris-HCl, 20 mM $MgCl_2$, 500 mM KCl, 2 mM $CaCl_2$, pH 7.5), and incubated at 37° C. for 30 min so that it was aggregated into fibrils. Then, actin depolymerization buffer (10 mM Tris-HCl, 0.2 mM $CaCl_2$, 0.2 mM ATP, pH 8.0) and PGAS of different concentrations were added for dilution so that it was depolymerized. A fluorescence microplate reader was set at an emission wavelength of 360 nm and an absorption wavelength of 410 nm and at a temperature of 37° C. It was thoroughly mixed and read once per min for continuous 30 min. The results show that, PGAS can significantly inhibit the actin depolymerization process in the cell-free system and exhibits dose dependence ($IC_{50}$ is 10.6 μM) (FIG. 9).

Figure 10:
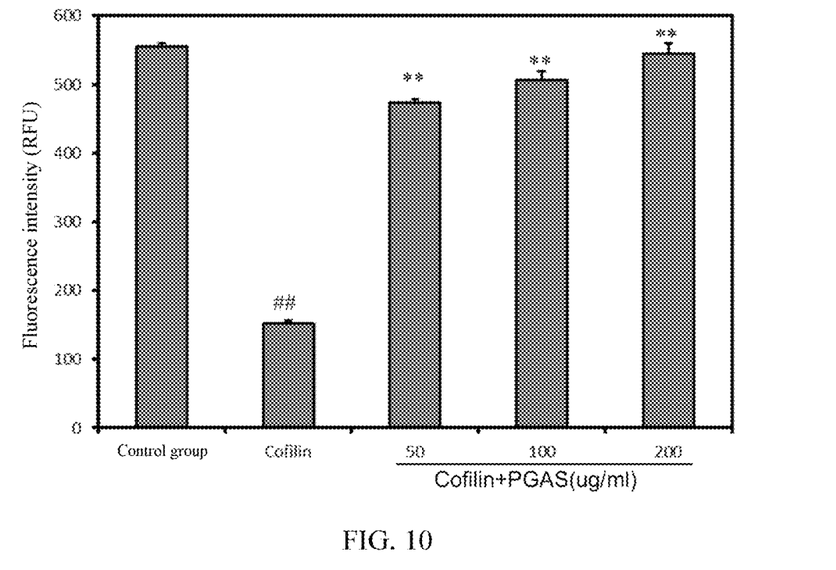
FIG. 10 shows the inhibition effect of a polygulonic acid sulfate of the present invention on actin depolymerising/cleaving activity of actin-depolymerising factor. ##P<0.01, Cofilin group v.s. control group; **P<0.01, medical group v.s. Cofilin group.

Example 11: Inhibition of PGAS on Actin Depolymerising/Cleaving Activity of Cofilin Polygulonic acid sulfate was coupled with Sepharose CL-4B to prepare an affinity chromatography column of polygulonic acid sulfate. Using this chromatography column, the binding proteins of polygulonic acid sulfate in lung cancer cell line A549 were extracted and separated. It was found by mass spectrometric identification that, cofilin is one of the proteins that binds strongly to polygulonic acid sulfate. Further studies show that polygulonic acid sulfate can significantly inhibit the actin depolymerising/cleaving activity of cofilin (FIG. 10). This indicates that polygulonic acid sulfate can bind to cofilin to inhibit the actin depolymerising/cleaving activity of cofilin, and thus function to inhibit the cell migration of tumor cells.

Example 12: Activity Determination of Sugar Components of PGAS

The anti-tumor activity of the PGAS sugar components prepared in Embodiment 3 was tested. It was found that, tetrasaccharide to dodecasaccharide components (corresponding to those with n being 2-10 in the general formula (I)) of the PGAS at an intravenous injection dose of less than 15 mg/kg have a T/C value of 30% or less on the growth of human breast cancer MDA-MB-435 orthotopic xenografts in nude mice, and have an inhibition rate of 95% or greater on lung metastasis thereof; hexasaccharide to decasaccharide components (in the general formula (I), n=4-8) at a dose of less than 10 mg/kg have a T/C value of 30% or less on the growth of human breast cancer MDA-MB-435 orthotopic xenografts in nude mice, and have an inhibition rate of 95% or greater on the lung metastasis thereof. The results are better when the sulfur content is 7-15 weight %, and are the best when being 9-13 weight %.

Example 13: Determination of Tumor Metastasis Inhibiting Activity of Sugar Components of PGAS The effect of different PGAS sugar components separated in Example 3 on tumor metastasis was detected with Transwell cell assay. Trypsin are used to digest breast cancer MDA-MB-435 cells that are passage cultured in vitro at exponentially grown stage, followed by washing with serum-free culture three times and diluted to $2 \times 10^6$/ml. 100 μl of the cell dilutions were added to the upper chambers of the wells in the Transwell cell, and 600 μl of 10% FBS-containing culture was added to the lower chambers, and 100 μg/ml of different PGAS components were added to both the upper and lower chambers. After the cells were incubated in a 5% $CO_2$-containing incubator at 37° C. for 12 h, the culture medium was removed, and the cells were fixed in a 90% ethanol solution for 30 min. The cells were stained with 0.1% crystal violet solution (0.1M boric acid, 0.1% (w/v) crystal violet, 2% ethanol) at room temperature for 10 min, rinsed with clear water, and wiped with cotton swabs to remove unmigrated cells in the upper layer. The cells were observed, photographed and recorded under a microscope. Finally, extraction was performed with 10% acetic acid solution at 100 μl/well for 10 min, the OD values were determined at 595 nm, and the migration inhibition rates of different sugar components on breast cancer cells were calculated.

Migration Inhibition Rate (%)=
$(1-OD_{treatment}/OD_{control}) \times 100\%$

Figure 11:
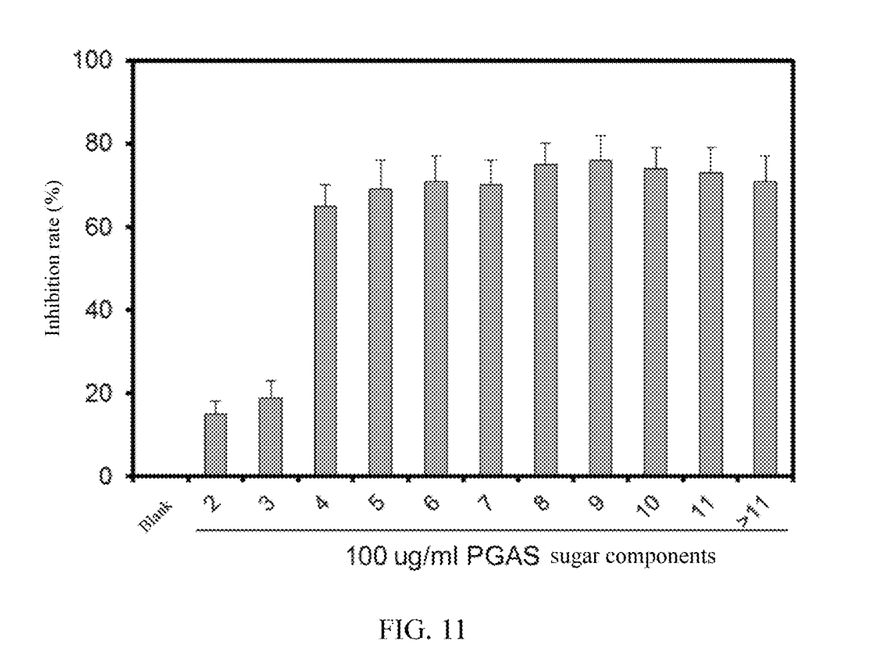
FIG. 11 shows the activity of tumor metastasis inhibition of respective components of a polygulonic acid sulfate of the present invention.

It was found that, MDA-MB-435 cells in the control group can freely migrate from the upper to lower champers within 12 hours along the concentration gradient of FBS. It can be seen from the photographic results of crystal violet staining that, different PGAS sugar components, ranging from tetrasaccharide (in the general formula I, n=2) to undecasaccharide (in the general formula I, n=9), and larger polysaccharides, can significantly inhibit the tumor cell migration, whereas disaccharide component (in the general formula I, n=0) and trisaccharide component (in the general formula I, n=1) have lower inhibition rates (FIG. 11), indicating that various PGAS components (particularly, from tetrasaccharide to undecasaccharide and larger polycomponent) has the metastasis inhibition effect of tumor cells.

Statistics Processing

The data above was subjected to statistical analysis with Statview software, the results were expressed as "Mean values±SE", and ANOVA was used for comparison.

According to the pharmacological results above, a pharmaceutical composition can be prepared using conventional formulation means by mixing an effective amount of a polygulonic acid sulfate of the present invention with a pharmaceutical carrier. The pharmaceutical composition can be used as tumor treatment drugs and tumor metastasis treatment drugs, and also can be used as angiogenesis inhibitors, heparanase inhibitors, C-Met enzyme inhibitors, microtubule polymerization inhibitors and actin-depolymerization inhibitors. The use of a polygulonic acid sulfate of the present invention in the preparation of a medicament for treating tumors and tumor metastasis is of very important significance.

The invention claimed is:

1. A polygulonic acid sulfate or pharmaceutically acceptable salt thereof, in which L-guluronic acid unit is linked by 1,4-glycosidic bonds with each other, with a hydroxyl located at position 1 of the reducing end, and the sugar rings completely sulfated at C-2 position, wherein the polygulonic acid sulfate has the following general formula (I):

wherein, n represents 0 or an integer of 1-23, $R_1$ is $SO_3H$, $R_2$, independent of one another, represents H or $SO_3H$, provided that the degree of sulfation calculated as the sulfur content of the polygulonic acid sulfate is 5 to 20 weight %.

2. The polygulonic acid sulfate or pharmaceutically acceptable salt thereof according to claim 1, wherein in the general formula (I), n is an integer of 2-13.

3. The polygulonic acid sulfate or pharmaceutically acceptable salt thereof according to claim 1, wherein the sulfur content is 7-15 weight %.

4. A method for preparing the polygulonic acid sulfate or pharmaceutically acceptable salt thereof according to claim 1, comprising:

reacting a polyguluronic acid as shown in the following structural formula (II) with a sulfonating reagent, followed by reduction via a reducing agent to give the polygulonic acid sulfate as shown in the general formula (I), (II)

in the structural formula (II), m represents 0 or an integer of 1-48;

(I)

in the general formula (I), n, $R_1$ and $R_2$ are as defined in claim 1.

5. The method according to claim 4, wherein the sulfonating reagent is chlorosulfonic acid; sulfonation temperature is 45-85° C.; reaction time is 1.5-4.5 hours, and the reducing agent is sodium borohydride, sodium cyanoborohydride, or nickel-hydride reagents.

6. A method of inhibiting tumor growth, tumor metastasis, angiogenesis, heparanase, C-Met enzyme, microtubule polymerization, actin-depolymerising factor activity, and/or actin-aggregation, comprising administering to a subject in need thereof a therapeutically effective amount of the polygulonic acid sulfate or pharmaceutically acceptable salt thereof according to claim 1.

7. The method according to claim 6, wherein the tumor is selected from the group consisting of liver cancer, stomach cancer, colorectal cancer, lung cancer, breast cancer, pancreas cancer, kidney cancer, bladder cancer, prostate cancer, melanoma, and brain cancer.

8. A pharmaceutical composition comprising a therapeutically effective amount of the polygulonic acid sulfate or pharmaceutically acceptable salt thereof according to claim 1.

9. A method of inhibiting tumor growth, tumor metastasis, angiogenesis, heparanase, C-Met enzyme, microtubule polymerization, actin-depolymerising factor activity and/or actin-aggregation comprising administering to a subject in need thereof a therapeutically effective amount of the pharmaceutical composition according to claim 8.

10. The polygulonic acid sulfate or pharmaceutically acceptable salt thereof according to claim 1, wherein in the general formula (I), n is an integer of 3, 4, 5, 6, 7 or 8.

11. The polygulonic acid sulfate or pharmaceutically acceptable salt thereof according to claim 1, wherein the sulfur content is 9-13 weight %.

12. The method according to claim 5, wherein the sulfonation temperature is 60-75° C.

13. The method according to claim 5, wherein the reaction time is 2-3.5 hours.

14. The method according to claim 5, wherein the reaction time is 3 hours.

* * * * *

UNITED STATES PATENT AND TRADEMARK OFFICE
CERTIFICATE OF CORRECTION

| | | |
|---|---|---|
| PATENT NO. | : 10,058,566 B2 | Page 1 of 1 |
| APPLICATION NO. | : 14/901297 | |
| DATED | : August 28, 2018 | |
| INVENTOR(S) | : Ding et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 179 days.

Signed and Sealed this
Twenty-seventh Day of August, 2019

Andrei Iancu
*Director of the United States Patent and Trademark Office*